(12) United States Patent  (10) Patent No.:  US 11,610,654 B1
White et al.  (45) Date of Patent:  Mar. 21, 2023

(54) DIGITAL FINGERPRINTING FOR AUTOMATIC GENERATION OF ELECTRONIC HEALTH RECORD NOTES

(71) Applicant: Zealth, Inc., San Mateo, CA (US)

(72) Inventors: Justin Stewart White, Sunnyvale, CA (US); Pranay Kapadia, Burlingame, CA (US); Adam Kessler Ting, San Francisco, CA (US)

(73) Assignee: Zealth, Inc., San Mateo, CA (US)

( * ) Notice: Subject to any disclaimer, the term of this patent is extended or adjusted under 35 U.S.C. 154(b) by 342 days.

(21) Appl. No.: 16/724,161

(22) Filed: Dec. 20, 2019

Related U.S. Application Data

(60) Provisional application No. 62/790,437, filed on Jan. 9, 2019.

(51) Int. Cl.
| | |
|---|---|
| *G16H 10/60* | (2018.01) |
| *G16H 50/70* | (2018.01) |
| *G06F 16/33* | (2019.01) |
| *G16H 70/60* | (2018.01) |
| *G16H 70/20* | (2018.01) |

(52) U.S. Cl.
CPC ......... *G16H 10/60* (2018.01); *G06F 16/3344* (2019.01); *G16H 50/70* (2018.01); *G16H 70/20* (2018.01); *G16H 70/60* (2018.01)

(58) Field of Classification Search
CPC ........ G16H 10/60; G16H 50/70; G16H 70/20; G16H 70/60; G06F 16/3344
See application file for complete search history.

(56) References Cited

U.S. PATENT DOCUMENTS

| | | | | |
|---|---|---|---|---|
| 6,047,259 | A * | 4/2000 | Campbell | G16H 40/20 |
| | | | | 705/3 |
| 6,684,276 | B2 * | 1/2004 | Walker | G16H 15/00 |
| | | | | 710/73 |
| 2008/0177537 | A1 * | 7/2008 | Ash | G16Z 99/00 |
| | | | | 704/235 |

(Continued)

OTHER PUBLICATIONS

Kannan, A. et al., "Semi-supervised learning for information extraction from dialogue," Interspeech, 2018, pp. 2077-2081.

(Continued)

*Primary Examiner* — Eliza A Lam
(74) *Attorney, Agent, or Firm* — Fenwick & West LLP

(57) ABSTRACT

A note automation server automatically generates medical notes for appointments between patients and physicians. The note automation server generates a fingerprint for each upcoming appointment between a patient and physician using information from an EHR system and information stored on the note automation server. The fingerprint includes information about the patient, including demographic information and medical history. The note automation server identifies an appropriate note template and billing codes for the appointment using the fingerprint and an audio file recorded by a physician during and/or after an appointment. The fingerprint, audio file, and note template are used complete of the medical note. The completed medical note and billing codes are exported to the EHR system, where it is accessed by the physician. The note automation server monitors the EHR system to see if the physician modified the medical note or a billing code.

20 Claims, 5 Drawing Sheets

(56) References Cited

U.S. PATENT DOCUMENTS

| | | | | |
|---|---|---|---|---|
| 2009/0182580 A1* | 7/2009 | Martin | ................... | G06Q 40/12 |
| | | | | 705/3 |
| 2011/0276348 A1* | 11/2011 | Ahn | ...................... | G16H 40/20 |
| | | | | 705/3 |
| 2016/0350496 A1* | 12/2016 | Cane | ...................... | G16H 70/20 |
| 2017/0308649 A1* | 10/2017 | Lodhia | ................... | G16H 15/00 |

OTHER PUBLICATIONS

Rajkomar, A. et al., "Scalable and accurate deep learning with electronic health records," NPJ Digital Medicine, 2018, pp. 1-10.

* cited by examiner

DIGITAL FINGERPRINTING FOR AUTOMATIC GENERATION OF ELECTRONIC HEALTH RECORD NOTES

CROSS-REFERENCE TO RELATED APPLICATIONS

This application claims the benefit of provisional U.S. Patent Application No. 62/790,437 filed on Jan. 9, 2019, which is incorporated herein by reference in its entirety for all purposes.

BACKGROUND

This description generally relates to electronic health records, and specifically to the automatic generation of medical notes.

Medical notes are generated by physicians during and after an appointment with a patient. Medical notes contain information about the patient's medical status, diagnoses, and treatment plans. Not only do physicians communicate with one another through such notes, but medical notes are also central to the overall scheme hospitals use to track activity and obtain reimbursement for their work through separate payment systems. Modern medical notes are often digital in format, being created, edited, and reviewed through Electronic Health Record (EHR) or Electronic Medical Record (EMR) systems.

Typically, physicians or scribes manually create medical notes during and after an appointment. However, medical note completion is bottlenecked by manual data entry. Physicians often complete medical notes after work hours, and spend, on average, two hours on data entry and administrative tasks for every hour of direct patient care. Also, for each appointment, physicians create medical notes from scratch. This can be repetitive for routine appointments such as annual physicals with general practitioners, bi-weekly appointments with OB/GYNs during pregnancies, and twice-annual dental visits. Because many physicians spend such a large fraction of their day merely capturing data from appointments rather than on patient care, physician quality of life is reduced and burnout is common. Further, manual medical note creation and data entry often lead to inaccuracies in the completed medical notes. These inaccuracies increase patient cost of care and negatively affect patient outcomes.

SUMMARY

A note automation server automatically generates medical notes for appointments between patients and physicians. The note automation server generates a fingerprint for each upcoming appointment between a patient and physician using information from an Electronic Health Record (EHR) system and information stored on the note automation server. The fingerprint includes information about the patient, including demographic information and medical history. The note automation server identifies an appropriate note template and billing codes for the appointment using the fingerprint, a scenario selected by the note automation server, and an audio file recorded by a physician during and/or after an appointment. A scenario captures the aggregate behavior of a physician given the physician's specialty, patient information (e.g., patient demographic information, medical history, insurance provider, reason for visit), and general reason for visit. Scenarios are generated in advance using historical encounter information between the physician and patients. Using the fingerprint, selected scenario, and note template, the note automation server generates a partially completed note for the appointment in advance of the appointment. In addition to generating a partially completed note, the note automation server predicts a set of billing codes for the upcoming appointment. Billing codes may be predicted using a prediction model or information from the selected scenario or fingerprint.

During and after the appointment, the physician records an audio file associated with the appointment. The audio file contains the physician's post-appointment dictation and may include a recording of the appointment. The note automation server pre-processes the audio file before obtaining a transcription of it. The transcription may be generated by a third-party transcription service or by the note automation server. The transcription of the audio file, the audio file, and the partially completed note are used to fill-in the remainder of the medical note. If billing codes were not previously predicted, the completed medical note and billing models are used to predict the billing codes. The completed medical note and billing codes are exported to the EHR system, where it is accessed by the physician. The note automation server monitors the EHR system to see if the physician modified the medical note or a billing code. If either the medical note or billing code were modified, the note automation server updates the training data used during scenario selection or in the training of the billing models. By automating the note generation process, the note automation server increases doctor efficiency, reduces patient cost of care, and improves patient outcomes.

DETAILED DESCRIPTION

Figure 1:
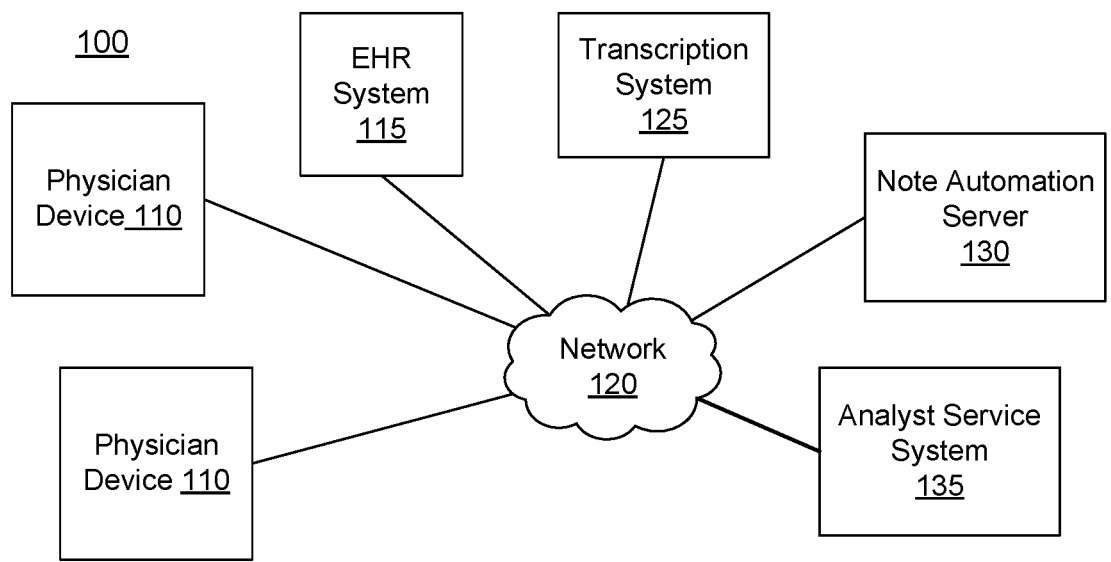
FIG. 1 is a block diagram of a system environment in which a note automation server operates, in accordance with an embodiment.

FIG. 1 is a block diagram of a system environment 100 for a note automation server 130. The system environment 100 shown by FIG. 1 comprises physician devices 110, an electronic health record (EHR) system 115, a network 120, a transcription system 125, the note automation server 130, and an analyst service system 135. In alternative configurations, different and/or additional components may be included in the system environment 100.

Physician devices 110 are computing devices capable of receiving user input, recording audio, as well as transmitting and/or receiving data via the network 120. In one embodiment, a client device 110 is a conventional computer system, such as a desktop or a laptop computer. Alternatively, a client device 110 may be a portable device having computer functionality, such as a smartwatch, personal digital assistant (PDA), a mobile telephone, a smartphone, or another suitable device. A physician device 110 is configured to communicate via the network 120. In one embodiment, a physician device 110 executes an application allowing a user of the physician device 110 to interact with the note automation server 130. For example, a physician device 110 executes a browser application to enable interaction between the physician device 110 and the note automation server 130 via the network 120. In another embodiment, a physician device 110 interacts with the note automation server 130 through an application programming interface (API) running on a native operating system of the physician device 110, such as IOS® or ANDROID™.

The physician devices 110 are configured to communicate via the network 120, which may comprise any combination of local area and/or wide area networks, using both wired and/or wireless communication systems. In one embodiment, the network 120 uses standard communications technologies and/or protocols. For example, the network 120 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 120 may be represented using any suitable format, such as hypertext markup language (HTML) or extensible markup language (XML). In some embodiments, all or some of the communication links of the network 120 may be encrypted using any suitable technique or techniques.

An EHR system 115 is coupled to the network 120 for communicating with the one or more physician devices 110 and the note automation server 130, which is described in detail below with reference to FIG. 2. In one embodiment, the EHR system 115 is a digital system that electronically stores health and medical records of patients. Through the EHR system 115, physicians and the note automation server 130 can access patients' demographic information, medical history, laboratory results, allergies, and the like. Further, the EHR system 115 may communicate information to the note automation server 130 and/or physician devices 110 such as patient appointment times, laboratory orders, immunization dates, etc.

The transcription system 125 is a third-party system that transcribes audio files generated on one or more physician devices 110. The transcription system 125 obtains an audio file associated with an appointment from the note automation server 130. Audio files are generated on physician devices 110 and pre-processed by the note automation server 130. In some embodiments, audio files contain a dictation performed by a physician on a physician device 110 after an appointment has ended. In other embodiments, audio files also contain a recording of the appointment. The transcription system 125 generates a transcription of the audio file. The transcription system 125 may generate diarized manuscripts of appointment recordings, when applicable. The transcription system 125 directs transcriptions of appointments to the note automation server 130. In some embodiments, a transcription system with similar functionality is integrated into the note automation server 130.

The analyst service system 135 obtains a transcription, audio recording, and partially completed note for each appointment from the note automation server 130. In some embodiments, the analyst service system 135 is a third-party system with operators who manually fill-in the partially completed note using the corresponding transcription and audio recording. In other embodiments, the analyst service system 135 is an online system that automatically completes the partially completed note. An analyst service system with similar functionality may be integrated into the note automation server 130.

Figure 2:
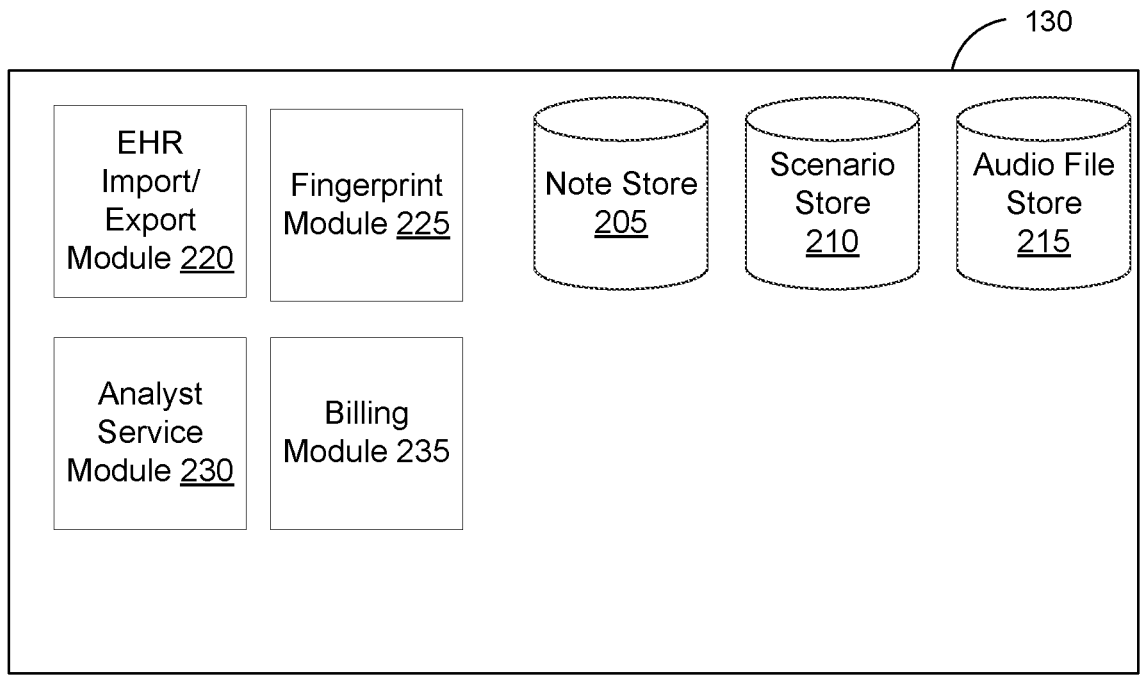
FIG. 2 is a block diagram a note automation server, in accordance with an embodiment.

FIG. 2 is a block diagram of an architecture of the note automation server 130. The note automation server 130 shown FIG. 2 includes a scenario store 205, a note store 210, an audio file store 215, an EHR import/export module 220, an analyst service module 230, a fingerprint module 225, and a billing module 235. In other embodiments, the note automation server 130 may include additional, fewer, or different components for various applications.

Each appointment between a physician and patient is associated with a note, which is stored in the note store 205. A note includes declarative information about the appointment that was shared explicitly by a patient and/or physician. A note may also include information that was obtained from the EHR system 115 using the EHR import/export module 220.

A note includes multiple data fields, each describing one or more attributes of the corresponding patient. Examples of information stored in a note include biographic, demographic, and other types of descriptive information, such as the chief complaint, history of present illness, results of a physical exam, a review of systems (ROS), family history, social history, lab results, diagnostics, imagery interpretations, assessment and plan, allergies, gestational age, current medication regime, and the like.

Each note also contains fields for a physician identifier, an evaluation and management (E&M) code, and a problem group. Physician identifiers are strings of letters and numbers that are used to uniquely identify a physician. In some embodiments, physician identifiers may be a human-recognizable name for the physician. E&M codes are used by physicians and EHR systems 115 to set a reimbursement rate for an appointment between the physician and a patient and any follow up care, treatments, or medications prescribed in association with the appointment. A problem group may include a diagnosis, an International Classification of Diseases 10$^{th}$ revision (ICD-10) code and zero or more orders that were made by a physician during the appointment.

The note store 210 also contains note templates that are used by the fingerprint module 225 and analyst service module 230 to generate completed notes for upcoming appointments. Note templates are created by the automation server 130 based on historical encounters between a physician and the patient and scenarios from the scenario store 210, discussed below. A note template contains empty data fields that are relevant to the patient and to the appointment. The number of data fields and the type of data fields contained in a note template may be specialty and/or physician specific. For example, many note templates contain empty data fields for demographic information, such as age and ethnicity, and health information, such as height and weight. Additional data fields can be added based on physician specialty. For example, a note template for an OB/GYN may also include data fields for number of previous births, gestational age, etc. As another example, a note template for a general practitioner may include data fields for dietary habits, vision tests, and hearing tests. Further, physicians may elect to use a note template depending on the nature of an appointment. For example, an OB/GYN physician may have a note template for an annual appointment with a patient between the ages of 20 and 30 years old that is insured with Medicaid. The same physician may use a different note template for a pregnancy appointment with a patient between the ages of 20 and 35 years old with a gestational age between 13 and 26 weeks and no previous live births. These two templates each contains data fields that are relevant to their respective appointments, e.g., physical exam results, treatment plans, depression screens, and the like.

While physicians may select a preferred note template, the automation server 130 may also select a note template for the physician. For example, the automation server 130 may select a note template based on a patient's demographic information and reason for visit. In other examples, the automation server 130 may select an appointment based on a patient's medical history and insurance provider. The automation server 130 increases physician efficiency and standardizes patient treatment by selecting an appropriate note template for the physician before each appointment.

A scenario captures the aggregate behavior of a physician given the physician's specialty, patient information (e.g., patient demographic information, medical history, insurance provider, reason for visit), and general reason for visit. Scenarios cover the common patterns that occur as a physician sees similar patients for similar reasons. In one embodiment, scenarios are manually generated by discussing common visit types and patient attributes and corresponding note templates, E&M codes, problems, orders, and ICD-10 diagnosis codes. In another embodiment, a physician's historical encounters are statistically analyzed to discover common patterns, with a set of scenarios derived by optimizing the number of correctly predicted note templates, E&M codes, problems, orders, and ICD-10 diagnosis codes for a given set of visit types and patient attributes against the actual note templates, E&M codes, problems, orders, and ICD-10 diagnosis codes. This optimization will also typically constrain the number of scenarios to avoid over-fitting.

A general reason for visit encompasses the patient's chief complaint. In one embodiment, it does not include secondary or unrelated complaints that were discussed during the appointment. For example, a patient may have an appointment for an annual check-up; however, during the appointment, the patient may ask a question about a rash. Here, the annual check-up is the general reason for visit and the rash is an unrelated complaint. The automation server 130 makes this distinction during scenario generation because it is unlikely that a significant fraction of patients visiting the physician for an annual check-up will also have a rash.

The automation server 130 uses scenarios to identify billing codes, problem groups, and/or note templates that are appropriate for an upcoming appointment. Scenarios may contain varying amounts and types of information. For example, the output for some scenarios may include one or more billings codes, a problem group, a note template, or a combination thereof. The amount and type of information varies based on the number of historical encounters between a physician and patients, the level of granularity chosen for each scenario, the practice or specialty of the physician, etc. For example, a patient may have a 10-week appointment with an OB/GYN. The patient is 27 years old, pregnant with her first child, and is 9 weeks into the gestation period. Based on historical encounters between the physician and other patients, there is a scenario that include a template for a 10-week appointment in which the patient is between 25 and 30 years old, pregnant with her first child, and is between 8-12 weeks pregnant. The scenario may also include the orders made by the OB/GYN common to the appointment encoded by that scenario (e.g., applying a 10-week sonogram order, taking a 10-week blood sample, etc.).

Audio files, stored in the audio file store 215, contain recordings of a physician's post-appointment dictation recorded on a physician device 110. In some embodiments, audio files also contain recordings of the appointment, requests from the physician to use a specific note template, and orders placed by the physician. Audio files are obtained from a physician device 110 once the physician marks the appointment as complete. Audio files may be stored as raw audio files, or they may be stored as anonymized recordings that have been pre-preprocessed by the analyst service module 230.

The EHR import/export module 220 imports and exports patient information to and from the EHR system 115. Specifically, the EHR import/export module 220 imports a patient's health record from the EHR system 115 once the patient checks in to an appointment with a physician. The EHR import/export module 220 directs the information from the EHR system 115 to the fingerprint module 225. The EHR import/export module 220 exports the output of the fingerprint module 225 to the EHR system 115.

Fingerprint Module

The fingerprint module 225 is configured to generate partially completed medical notes for each appointment between a patient and physician. Examples of billing codes include E&M codes, ICD-10 codes, etc. In some embodiments, the fingerprint module 225 also generates a set of billing codes and/or orders associated with upcoming appointment. Partially completed medical notes are directed to the analyst service module 230 that is configured to complete the medical notes. Billing codes and orders are directed to the EHR import/export module 220 that exports them to the EHR system 115. From the EHR system 115, physicians may view and modify billing codes and orders.

The fingerprint module 225 generates a partially completed note for each upcoming appointment between a physician and patient by creating a fingerprint of the appointment A fingerprint is an object that contains data fields associated with patient information and the upcoming appointment. The amount of information included in a fingerprint may vary based on the patient's health record in the EHR system 115, information provided at check-in, specialty of the physician, physician's preferences, etc. For each upcoming appointment, the fingerprint module 225 obtains patient information and appointment information from the EHR import/export module 220. Patient information may include patient demographic information, insurance provider, and historical encounters between the patient and physician. Appointment information includes the patient's reason for visit, chief complaint, appointment start time, etc. In some embodiments, the fingerprint module 225 obtains patient information and appointment information after receiving an indication from the EHR system 115 that a patient has checked-in to an appointment. In other embodiments, the fingerprint module 225 obtains information when a patient schedules an appointment with a physician, during the appointment, after the appointment, and the like. The fingerprint may also include binary flags that indicate whether the patient is a new patient and whether the appointment is a post-surgery follow-up visit.

The fingerprint module 225 inputs the patient and appointment information into the object to generate a fingerprint for an appointment. The fingerprint module 225 uses the fingerprint to select a scenario or set of scenarios that is used by the automation server 130 to complete a medical note, set billing codes, and/or generate orders. The fingerprint module 225 accesses scenarios from the scenario store 205 and selects a scenario or set of scenarios for the appointment. Scenarios are selected by comparing the fingerprint to the scenarios stored in the scenario store 210 using a set of selection rules. In some embodiments, scenarios are filtered twice before choosing a scenario or set of scenarios that is used by the automation server 130. For example, during a first round of filtering, a set of candidate scenarios is identified based on a first set of rules. Examples of rules include filtering scenarios based on physician identifier, patient age, etc. A scenario or set of scenarios is then selected from the set of candidate scenarios based on a second set of rules during a second round of filtering. Examples of rules may include insurance provider, laboratory orders, etc. In other embodiments, a candidate scenario is selected in a single selection process, using three or more rounds of filtering, etc. Any remaining scenarios after all rules have been evaluated are applied to the note for the corresponding appointment. Scenarios that have a note template as the output result in the corresponding note template being applied to the note. If the scenario has a set of problem groups as its output, then the problem groups are added to the note. If the scenario has an E&M code as its output, then the E&M code is set on the note.

The fingerprint module 225 may also use rules to pre-order tests for the patient on behalf of a physician. In some embodiments, the order is directly sent to a laboratory or testing facility prior to an appointment. In other embodiments, the physician accepts the order on a physician device 110 during or after an appointment. Tests can include tests for blood work, x-rays, MRIs, mammograms, CT scans, and the like. The fingerprint module 225 may add an order for a test to the patient's chart based on information retrieved from the selected scenario, based on the patient's medical history, based on the patient's reason for visit, etc. For example, there may be an order that is applied once, and the fingerprint module 225 examines the patient's record to determine if the order has been applied during previous encounters with the physician. For instance, an OB/GYN may have a set of orders for patients with an 18 weeks gestational age that is applied when a patient comes for an appointment any time between 16 and 20 weeks into their gestational period. If the patient comes for an appointment with the OB/GYN at week 16, and the order hasn't been applied in previous visits, the 18-week order set is pre-ordered by the note automation server 130. If the same patient comes in at week 17, the order is not applied because patient's record indicates the 18-week order set has been previously applied.

In another example, a patient may have an appointment with a physician to check out a potentially broken leg. The fingerprint module 225 is configured to generate an order for x-rays based on information in the selected scenario and the patient's reason for visit, e.g., potentially broken leg. The order may include varying amounts of information based on the information received from the patient at check-in and based on the selected scenario. For example, the patient may have specified which leg is potentially broken, and the selected scenario may indicate that the physician typically requests x-rays from three points of view when a broken leg is examined. In some embodiments, if not enough information is available to complete the order, the fingerprint module 225 may send a partially completed order to the physician on the physician device 110. The physician can complete the order during or after the appointment using the partially completed order. In other embodiments, the fingerprint module 225 can send the partially completed order to the analyst service module 230 that is configured to complete the order using the audio file associated with the appointment. In other embodiments, the partially completed order is exported to the EHR system 115 by the EHR import/export module 220. Completed orders are exported to the EHR system 115, from which the laboratories and testing facilities can receive and process the orders.

When the selected scenario or set of scenarios includes a note template, the fingerprint module 225 selects a note template from the note store 205 that is associated with the selected scenario or set of scenarios, and inputs the fingerprint and data fields from the selected scenario into the note template. When the selected scenario does not include a note template, a generic note template may be used and is filled-in using the fingerprint and selected scenario or set of scenarios. Alternatively, the physician may indicate in the audio file which note template to use for an appointment. In some embodiments, some of the data fields from the selected scenario are not directly inputted into a note. For example, billing codes and problem groups from the selected scenario may be exported directly to the EHR system 115 via the EHR import/export module 220. If the selected scenario or set of scenarios is missing one or more billings codes, billing codes for the appointment are generated by the billing module 235, discussed below. The fingerprint module 225 directs the partially completed note to the analyst service module 230. In some embodiments, the fingerprint module 225 also directs any partially completed orders to the analyst service module 230.

Analyst Service Module

The analyst service module 230 completes a medical note for each appointment using the partially completed note generated by the fingerprint module 225. The analyst service module 230 may also generate orders for an appointment. For example, if one or more orders are not completed by the fingerprint module 225, the analyst service module 230 completes the one or more orders. The analyst service module 230 directs the completed orders to the EHR import/export module 220 that will export them to the EHR system 115.

The analyst service module 230 receives the partially completed note from the fingerprint module 225 and an audio file associated with an appointment from the audio file store 215. The analyst service module 230 preprocesses the audio file. Examples of pre-processing steps include transcoding, padding, and normalizing the audio file. More, fewer, or different pre-processing steps may be applied to the audio file to prepare the audio file for anonymization and transcription. The analyst service module 230 may direct the pre-processed audio file to the transcription system 125. The analyst service module 230 may also direct the pre-processed audio file to a transcription system integrated into the note automation server 130. The analyst service module 230 also processes physician's request to use a specific note template for the appointment and orders made by the physician during an appointment (e.g., x-rays, blood work, etc.)

The analyst service module 230 obtains the transcription of the appointment and directs the transcription, note template, and audio file to the analyst service system 135 that fills-in the note. The analyst service module 230 obtains the filled-in note and verifies the information has been properly added to the note. The analyst service module 230 also includes information that is specific to the physician (e.g., physician referrals, laboratory locations, local pharmacies, etc.). The completed note is exported by the EHR import/export module 220 to the EHR system 115.

Billing Module

The billing module 235 predicts billing codes for upcoming appointments based on the fingerprint generated by the fingerprint module 225 and the selected scenario or set of scenarios. The billing module 235 may also use the audio file associated with the appointment to generate one or more billing codes. Examples of billing codes include E&M codes, ICD-10 codes, etc. In some embodiments, the billing module 235 predicts billing codes and problem groups for each appointment. For example, when a scenario selected by the fingerprint module 230 does not include one or more billing codes for an appointment, the billing module 235 generates the one or more billing codes. In some embodiments, the billing module 235 includes a GRU model that is used to generate ICD-10 codes. In some embodiments, the billing module 235 includes a boosted tree model that is used to generate E&M codes. Different models, such a random forest models, may also be used to predict billing codes and problem groups. The models are trained and validated using previously-completed notes from the note store 210. In other embodiments, e.g., when a selected scenario or set of scenarios includes all of the billing codes, the billing module 235 may not be used to generate billing codes for the appointment. In some embodiments, the billing module 235 is used to compare a set of predicted billing codes to the billing codes from the scenario. Here, the billing module 235 can determine how well the selected scenario or set of scenarios matches the corresponding appointment.

Generating Completed Medical Notes

Figure 3:
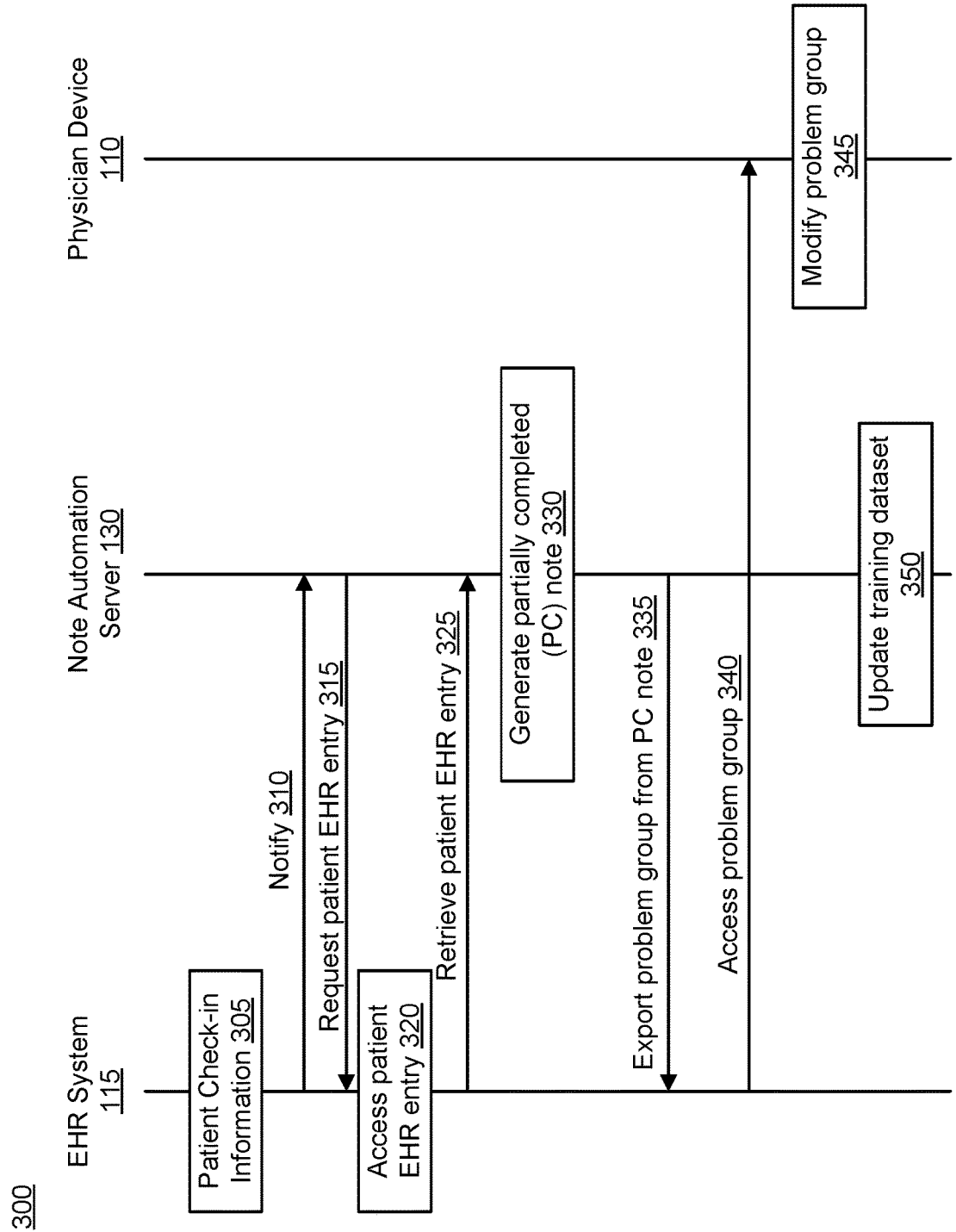
FIG. 3 is an interaction diagram that illustrates a method of generating a partially completed note associated with an appointment between a patient and a physician.

FIG. 3 is an interaction diagram that illustrates a method 300 of generating a partially completed note for an appointment between a patient and a physician. The patient checks in 305 to an appointment with the physician. The EHR system 115 may notify the note automation server 130 of the check-in. The note automation server 130 may also continuously monitor the EHR system 115 in anticipation of appointment check-ins. The note automation server 130 requests 315 the patient's entry in the EHR system 115. The EHR system 115 accesses 320 the patient entry, and the note automation server 130 retrieves 325 it. Using the patient entry, scenarios stored in the scenario store 210, and a note template from the note store, the note automation server 130 generates 330 a partially completed note for the appointment. The note automation server 130 exports 335 problem groups and billing codes to the EHR system 115. The physician can access 340 and modify 345 the problem group with a physician device. The note automation server 130 monitors the EHR system 115 to see if the physician has modified the problem group and/or billing codes. If the physician has made a modification, the note automation server 130 may update 350 the training dataset used to select a scenario.

Figure 4:
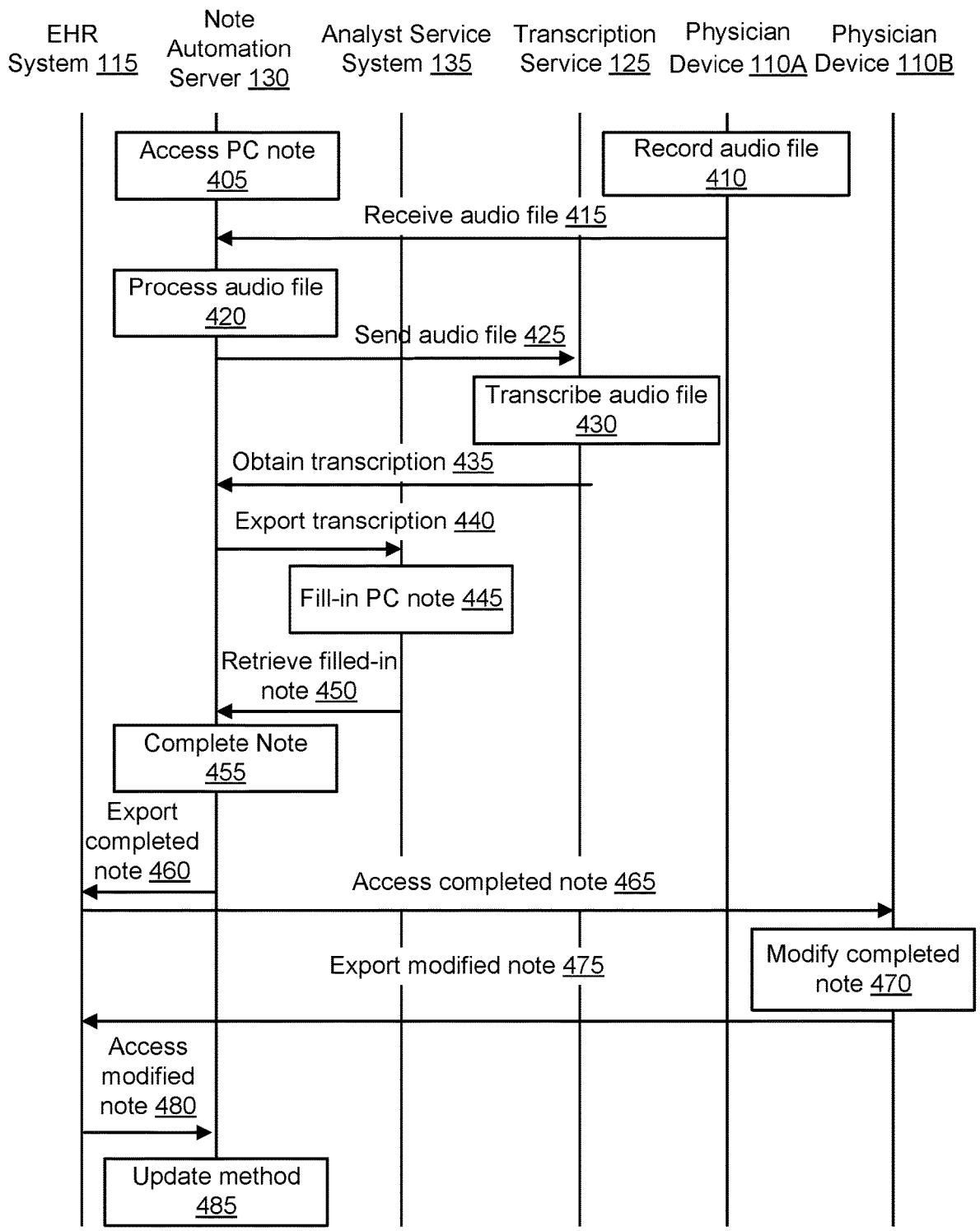
FIG. 4 is an interaction diagram that illustrates a method of generating a completed note from audio recordings of an appointment between a patient and a physician.

FIG. 4 is an interaction diagram that illustrates a method 400 of generating a completed note from audio recordings of an appointment between a patient and a physician. The note automation server 130 accesses 405 a partially completed note generated using the method discussed in FIG. 3. The physician records 410 an audio file for the appointment, which includes a dictation of the appointment, on a physician device 110A (e.g., a portable recording device, a smartwatch, etc.). The audio file may also contain a recording of the appointment. The note automation server 130 receives 415 the audio file from the physician device and processes 420 it. The note automation server 130 sends 425 the audio file to a transcription service 125 that transcribes 430 the audio file. In some embodiments, the note automation server 130 transcribes the audio file internally. The note automation server 130 obtains 435 the transcription of the audio file and exports 440 it to an analyst service system 135. The note automation server 130 also directs the partially completed note and audio file to the analyst service system 135. In some embodiments, a similar analyst service system is integrated into the note automation server 130. The analyst service system 135 fills-in 445 the partially completed note using the materials obtained from the note automation server 130. The note automation server 130 retrieves 450 the filled-in note and completes 455 it. The note automation server 130 completes 455 the note by adding local information that was not easily accessed by the analyst service system, making corrections to the note, etc. The note automation server 130 exports 460 the note to the EHR system 115, where the physician can access 465 the note. The physician may modify 470 the completed note on a physician device 110 (e.g., a laptop, desktop, tablet, etc.). For example, the physician can update orders that were made during the appointment, modify problem groups or billing codes, etc. The physician exports 475 the modified note to the EHR system 115. The note automation server 130 continuously monitors the EHR system 115 for a predetermined amount of time (e.g., two weeks, a month, etc.) to see if the physician has modified the note. If the physician modified 470 the note, the note automation server 130 accesses 480 the modified note and updates the method of completing a note.

Figure 5:
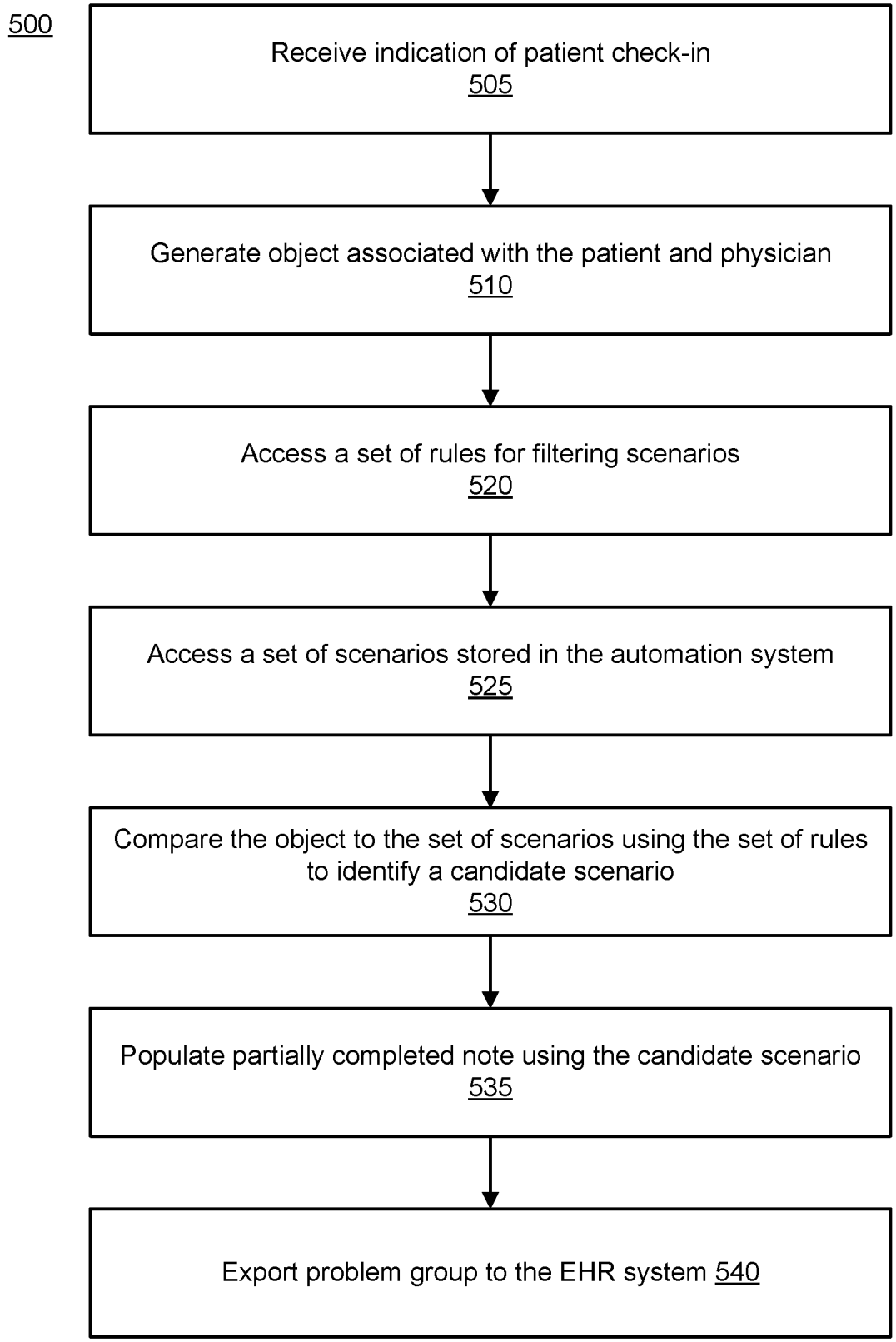
FIG. 5 is a flowchart that illustrates a method of generating a partially completed note associated with an appointment between a patient and a physician.

FIG. 5 is a flowchart that illustrates a method 500 of generating a partially completed note associated with an appointment between a patient and a physician. An indication that a patient has checked-in to an appointment with a physician is received 505. The indication may be received 505 from an EHR system 115 or from a physician device 110. An object (fingerprint) associated with the patient and physician using information retrieved from the EHR system 115 and/or information from the physician device 110 is generated 510. Information retrieved from the EHR system may include information about the appointment, historical encounters between the patient and physician associated with the appointment, demographic and biological information, etc. A set of rules used for filtering scenarios is accessed 520. Rules are generated and trained in advance of appointments by the note automation server 130. Rules may be generated using historical encounters between patients and physicians. A set of scenarios stored 525 in the note automation server 130 is accessed 525. The object is compared 530 to the set of scenarios using the set of rules to identify a scenario or set of scenarios and select a note template or templates. The note template is populated 535 using the scenario and object. A problem group, identified using the selected scenario or one or more billing models, is exported 540 to the EHR system.

Figure 6:
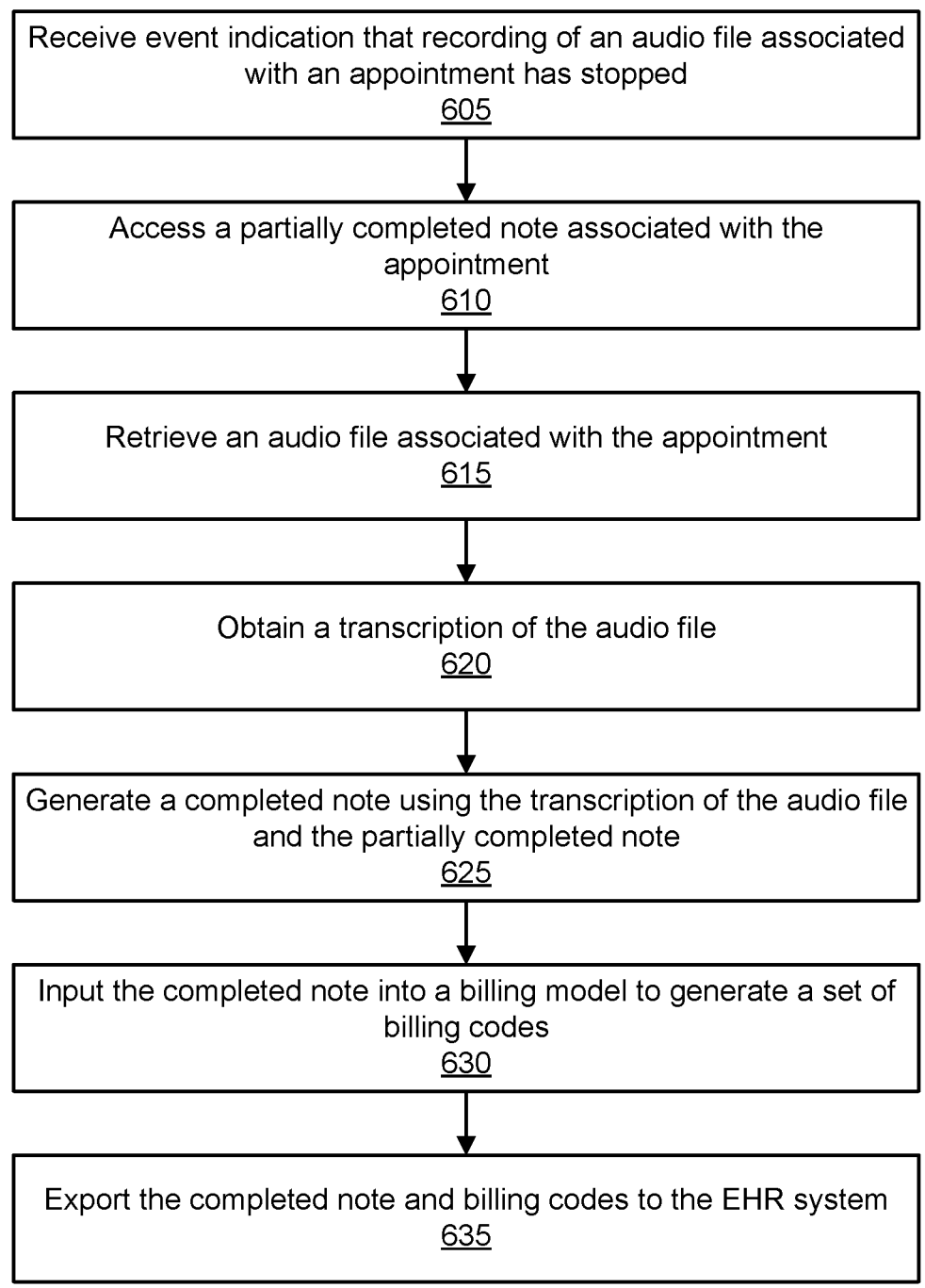
FIG. 6 is a flowchart that illustrates a method of generating a completed note from audio recordings of an appointment between a patient and a physician.

FIG. 6 is a flowchart that illustrates a method 600 of generating a completed note from audio recordings of an appointment between a patient and a physician. An event indication is received 605 that recording of an audio file associated with an appointment has ended. In some embodiments, the audio file contains a dictation from a physician of the appointment. In other embodiments, the audio file also contains a recording of the appointment. The partially completed note generated using an object (fingerprint) of the appointment and a scenario or set of scenarios is accessed 610. The audio file associated with the appointment is retrieved 615 from a portable recording device. A transcription of the audio file is obtained 620. In some embodiments, the transcription contains a diarized manuscript of the appointment recording. A completed note is generated 625 using the transcription of the audio file and the partially completed note. The completed note is inputted 630 into a billing model to generate a set of billing codes for the appointment. The completed note and billing codes are exported 635 to the EHR system.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for automating completion of a medical note for an appointment between a physician and a patient, the method comprising:
    prior to occurrence of the appointment, by a note automation server, deriving a set of scenarios for common patterns for appointments with similar patients having similar primary reasons for the appointments and deriving a set of selection rules for selecting scenarios for appointments;
    generating, by the note automation server, a digital fingerprint object for the appointment between the patient and the physician, wherein the object includes a set of entries comprising:
        a patient identifier for the patient provided by an electronic health record (EHR) system,
        a physician identifier for the physician provided by the EHR system,
        patient demographic information,
        a primary reason for the appointment, and
        a medical history of the patient
    comparing, at the note automation server, the digital fingerprint object to the set of scenarios to select a scenario from the set of scenarios based on the set of selection rules, the selected scenario including a note template; and
    at least partially completing a medical note for the appointment by populating the note template based on entries from the digital fingerprint object, including predicting entries for billing, diagnosis and physician order information for the appointment, wherein predicting at least one of the entries uses at least one of a GRU model, a boosted tree model and a random forest model.

2. The method of claim 1, wherein a plurality of the scenarios comprise entries determined based on historical encounters between a different physician and a different plurality of patients.

3. The method of claim 1, wherein comparing further comprises:
    identifying, by the note automation server, candidate scenarios by comparing the set of scenarios to the digital fingerprint object using a first subset of the set of selection rules; and
    selecting one of the candidate scenarios by comparing the candidate scenarios to the digital fingerprint object using a second subset of the set of selection rules.

4. The method of claim 1, wherein the set of scenarios are compared to the digital fingerprint object using a text matching technique.

5. The method of claim 1, wherein the set of scenarios are compared to the digital fingerprint object using a model, wherein entries from the set of scenarios are model inputs.

6. The method of claim 3, wherein the first subset of selection rules includes a rule based on a physician identifier and a rule based on a patient age, and wherein the second subset of selection rules includes a rule based on a patient insurance provider.

7. The method of claim 1, further comprising:
    generating a physician order based on one or more entries of the selected scenario and a subset of the set of selection rules; and
    sending the physician order to the EHR system.

8. The method of claim 1, further comprising:
    receiving, at the note automation server, a modification indication that the physician has modified an entry of the partially completed medical note; and
    responsive to the indication, updating the method of selecting a scenario based on the modification.

9. The method of claim 1, wherein the set of entries in the digital fingerprint object further comprises a patient insurance provider, and demographic information.

10. The method of claim 1, wherein the predicted billing entry includes at least one of an Evaluation and Management (E&M) code and an International Classification of Diseases $10^{th}$ revision (ICD-10) code.

11. A non-transitory computer-readable storage medium for automating completion of a medical note for an appointment between a physician and a patient containing computer program code for:
    prior to occurrence of the appointment, by a note automation server, deriving a set of scenarios for common patterns for appointments with similar patients having similar primary reasons for the appointments and deriving a set of selection rules for selecting scenarios for appointments;
    generating, by the note automation server, a digital fingerprint object for the appointment between the patient and the physician, wherein the object includes a set of entries comprising:
        a patient identifier for the patient provided by an electronic health record (EHR) system,
        a physician identifier for associated with the physician provided by from the EHR system,
        patient demographic information,
        a primary reason for the appointment, and
        a medical history of the patient
    comparing, at the note automation server, the digital fingerprint object to the set of scenarios to select a scenario from the set of scenarios based on the set of selection rules, the selected scenario including a note template; and
    at least partially completing a medical note for the appointment by populating the note template based on entries from the digital fingerprint object, including predicting entries for and billing, diagnosis and physician order information for the appointment, wherein predicting at least one of the entries uses at least one of a GRU model, a boosted tree model and a random forest model.

12. The non-transitory computer-readable medium of claim 11, wherein comparing further comprises:
identifying, by the note automation server, candidate scenarios by comparing the set of scenarios to the digital fingerprint object using a first subset of the set of selection rules; and
selecting one of the candidate scenarios by comparing the candidate scenarios to the digital fingerprint object using a second subset of the set of selection rules.

13. The non-transitory computer-readable medium of claim 11, further comprising:
generating a physician order based on one or more entries of the selected scenario and a subset of the set of selection rules; and
sending the physician order to the EHR system.

14. The non-transitory computer-readable medium of claim 11, further comprising:
receiving, at the note automation server, a modification indication that the physician has modified an entry of the partially completed medical note; and
responsive to the indication, updating the method of selecting a scenario based on the modification.

15. The non-transitory computer-readable medium of claim 11, wherein the predicted billing entry includes at least one of an Evaluation and Management (E&M) code and an International Classification of Diseases $10^{th}$ revision (ICD-10) code.

16. A system for automating completion of a medical note for an appointment between a physician and a patient, the system comprising:
a processor configured to execute instructions; and
a non-transitory computer-readable medium containing instructions executed by the processor, the instructions causing the processor to:
prior to occurrence of the appointment: derive a set of scenarios for common patterns for appointments with similar patients having similar primary reasons for the appointments and derive a set of selection rules for selecting scenarios for appointments;
generate a digital fingerprint object for the appointment between the patient and the physician, wherein the object includes a set of entries comprising:
a patient identifier for the patient provided by an electronic health record (EHR) system,
a physician identifier for the physician provided by the EHR system,
patient demographic information,
a primary reason for the appointment, and
a medical history of the patient
compare the digital fingerprint object to the set of scenarios to select a scenario from the set of scenarios based on the set of selection rules, the selected scenario including a note template; and
at least partially complete a medical note for the appointment by populating the note template based on entries from the digital fingerprint object, including predicting entries for billing, diagnosis and physician order information for the appointment, wherein predicting at least one of the entries uses at least one of a GRU model, a boosted tree model and a random forest model.

17. The system of claim 16, wherein comparing further comprises:
identifying candidate scenarios by comparing the set of scenarios to the digital fingerprint object using a first subset of the set of selection rules; and
selecting one of the candidate scenarios by comparing the candidate scenarios to the digital fingerprint object using a second subset of the set of selection rules.

18. The system of claim 16, wherein the instructions further cause the processor to:
generate a physician order based on one or more entries of the selected scenario and a subset of the set of selection rules; and
send the physician order to the EHR system.

19. The system of claim 16, wherein the instructions further cause the processor to:
receive a modification indication that the physician has modified an entry of the partially completed medical note; and
responsive to the indication, update the method of selecting a scenario based on the modification.

20. The method of claim 1, wherein:
deriving the set of scenarios and the set of selection rules comprises:
statistically analyzing the physician's historical appointments with multiple patients to discover the common patterns for appointments with similar patients having similar primary reasons for the appointments; and
deriving the set of scenarios and the set of selection rules, based on the discovered common patterns and based on a metric for correctly predicting medical notes, diagnoses and the physician's orders for the appointments; and
the physician's behavior for the appointment is expected to be statistically similar to the physician's aggregate behavior for the selected scenario.

* * * * *